(12) United States Patent
Bowser et al.

(10) Patent No.: US 6,357,681 B1
(45) Date of Patent: Mar. 19, 2002

(54) SPRING CUTTER-SEPARATOR

(75) Inventors: Timothy J. Bowser, Stillwater, OK (US); Davey Joe Vadder, Springfield, VA (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 0 days.

(21) Appl. No.: 09/618,313

(22) Filed: Jul. 18, 2000

(51) Int. Cl.⁷ ................................................ B02C 19/00
(52) U.S. Cl. ........................ 241/82.3; 241/94; 241/283
(58) Field of Search ............................ 241/94, 74, 283, 241/82.3

(56) References Cited

U.S. PATENT DOCUMENTS 4,340,184 A * 7/1982 Poss .......................... 241/82.3
5,580,305 A * 12/1996 McFarland .................. 241/74

* cited by examiner

*Primary Examiner*—Mark Rosenbaum
(74) *Attorney, Agent, or Firm*—Fellers, Snider, Blankenship, Bailey & Tippens, P.C.

(57) ABSTRACT

A cutter-separator. Product is fluidized under pressure, forced through the bore of a spring and thence through the gaps between the coils of the spring while in its extended condition. When the spring returns to its compressed, or relaxed, condition the product which has been forced through the coils is reduced in size (i.e., cut, partially cut, or mashed, as desired) by the spring. Contaminants which are too large to pass between the coils are ultimately carried to the end of the spring, downstream from the product flow, where they are discharged.

10 Claims, 10 Drawing Sheets

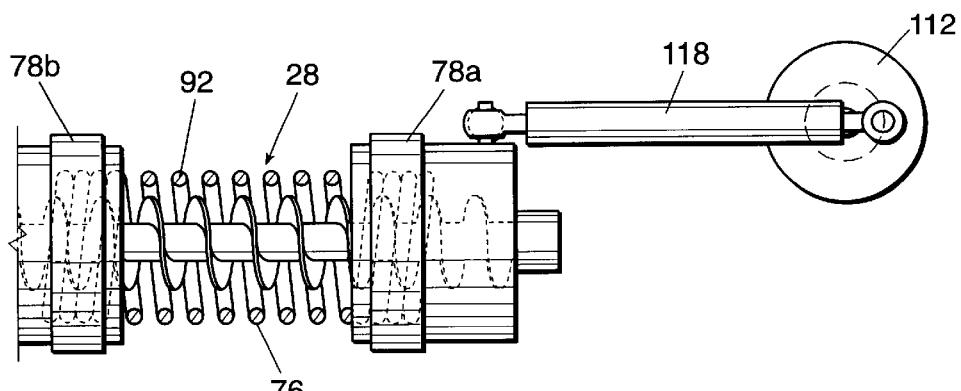
*Fig. 12*
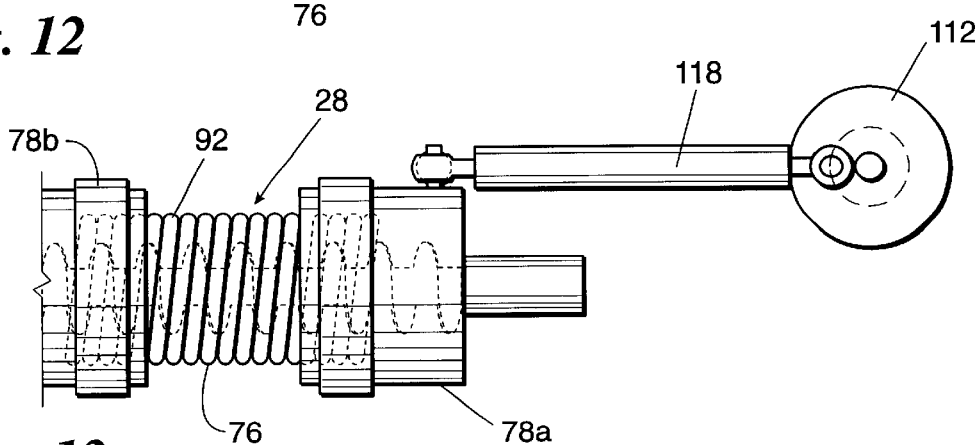
*Fig. 13*
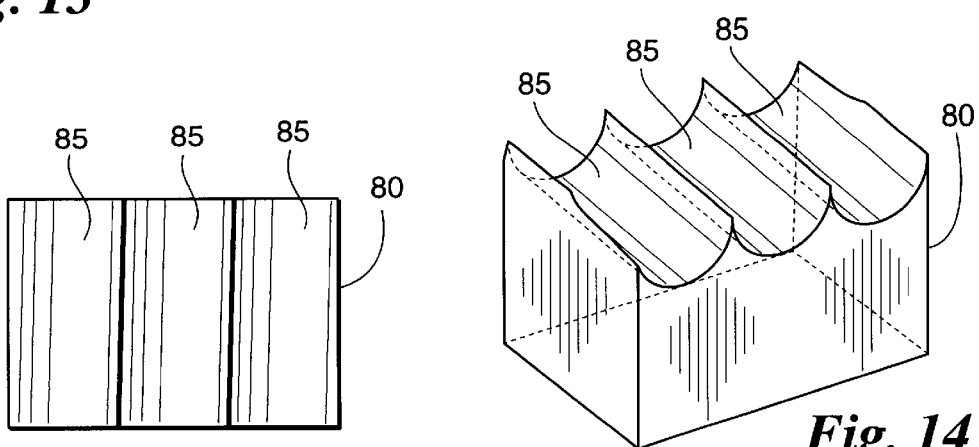
*Fig. 14*
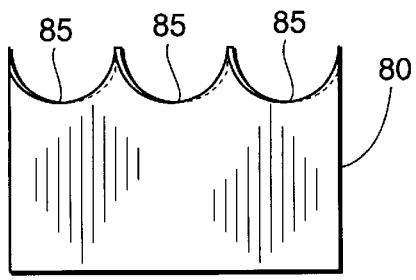
*Fig. 17*
*Fig. 15*
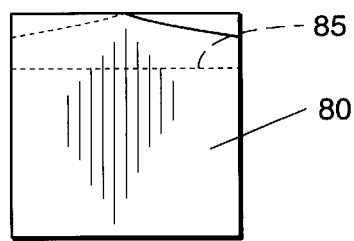
*Fig. 16*

SPRING CUTTER-SEPARATOR

BACKGROUND OF THE INVENTION

1. Field of the Invention

This invention relates generally to a cutter-separator for food and agricultural products. More particularly, but not by way of limitation, the present invention relates to a device in which material is supplied under pressure to the inner bore of an oscillating spring wherein desirable product is extruded through the space between the coils when the spring is in a stretched state, thereby separating desirable product from undesirable matter, and size reduction of the desirable product thus separated, is performed by the action of the coils when the spring is in a compressed state.

2. Background

Traditionally, cutting, grinding and size reduction processes used for food and agricultural products involve the use of devices with rotating blades, plates, cones, or rollers with fixed orifice plates or screens and a feed mechanism. Common names for these types of machines are hammer mill, grinder, crusher, cutter, attrition mill, and comminuter. Many of these devices provide no mechanism for separating foreign matter such as bone, plastic, metal, or glass from the product. In these cases, contaminants are processed along with the product making them increasingly difficult to detect and remove.

Equipment of this type often has dangerous moving parts and hazardous, sharp blades. Many of the blades used in such equipment are sharp enough to cut, even when motionless, posing hazards to sanitation and maintenance crews. In addition, some grinders utilize high-speed, rotating shafts, close tolerance blades, and stators. These parts are expensive to replace and costly to maintain. An ideal size reducer would have the following operating characteristics: (1) it would produce uniform product size; (2) its use would result in minimal temperature rise in the product; (3) it would require minimal power to operate; and (4) it would provide trouble free-operation.

It is thus an object of the present invention to provide a cutter-separator which will reliably separate foreign material from desirable product prior to the size reduction process.

It is a further object of the present invention to provide a cutter-separator which avoids the use of hazardous parts and thus, poses a reduced physical threat to the operator or maintenance personnel.

It is another object of the present invention to provide a cutter-separator which, in operation, will produce product of uniform size.

It is yet another object of the present invention to provide a cutter-separator which, in operation, will produce minimal temperature rise in the product.

SUMMARY OF THE INVENTION

These and other objects and advantages are achieved in a cutter-separator which uses an oscillating spring to first separate contaminants from the product and then to reduce the product to a uniform size.

In the inventive cutter-separator, product is fluidized under pressure, forced through the bore of a spring and thence through the gaps between the coils of the spring while in its extended condition. When the spring returns to its compressed, or relaxed, condition the product which has been forced through the coils is reduced in size (i.e., cut, partially cut, or mashed, as desired) by the spring. Contaminants which are too large to pass between the coils are ultimately carried to the end of the spring, downstream from the product flow, where they are discharged.

In one embodiment of the inventive device, pressure is obtained by an auger which rotates inside the bore of an oscillating spring. As product is forced into the spring by the auger, pressure causes the product to fluidize and pass between the coils of the spring while separated. As the spring returns to its compressed state, the product is cut to size. Separation is accomplished because the pressure is insufficient to fluidize dense particles, i.e., bone chips, glass, metal, and the like. These dense particles are carried along the axis of the auger and discharged through an opening in a backpressure plate. Contaminants will not pass between the spring gaps as long as they are larger than the gaps. This results in a product stream, exiting through the spring coils, which is separate from the contaminant stream, exiting at the backpressure plate.

A better understanding of the present invention, its several aspects, and its objects and advantages will become apparent to those skilled in the art from the following detailed description, taken in conjunction with the attached drawings, wherein there is shown and described the preferred embodiment of the invention, simply by way of illustration of the best mode contemplated for carrying out the invention.

BRIEF DESCRIPTION OF THE DRAWINGS

FIG. 12 provides a side view of the spring assembly and camshaft with the spring in its fully extended state.

FIG. 13 provides a side view of the spring assembly and camshaft with the spring in its fully compressed state.

FIG. 14 provides a perspective view of a wedge block as incorporated in the inventive spring cutter-separator.

FIG. 15 provides a side elevational view of a wedge block as incorporated in the inventive spring cutter-separator.

FIG. 16 provides an front view of a wedge block as incorporated in the inventive spring cutter-separator.

FIG. 17 provides a top view of a wedge block as incorporated in the inventive spring cutter-separator.

DETAILED DESCRIPTION OF THE PREFERRED EMBODIMENT

Figure 1:
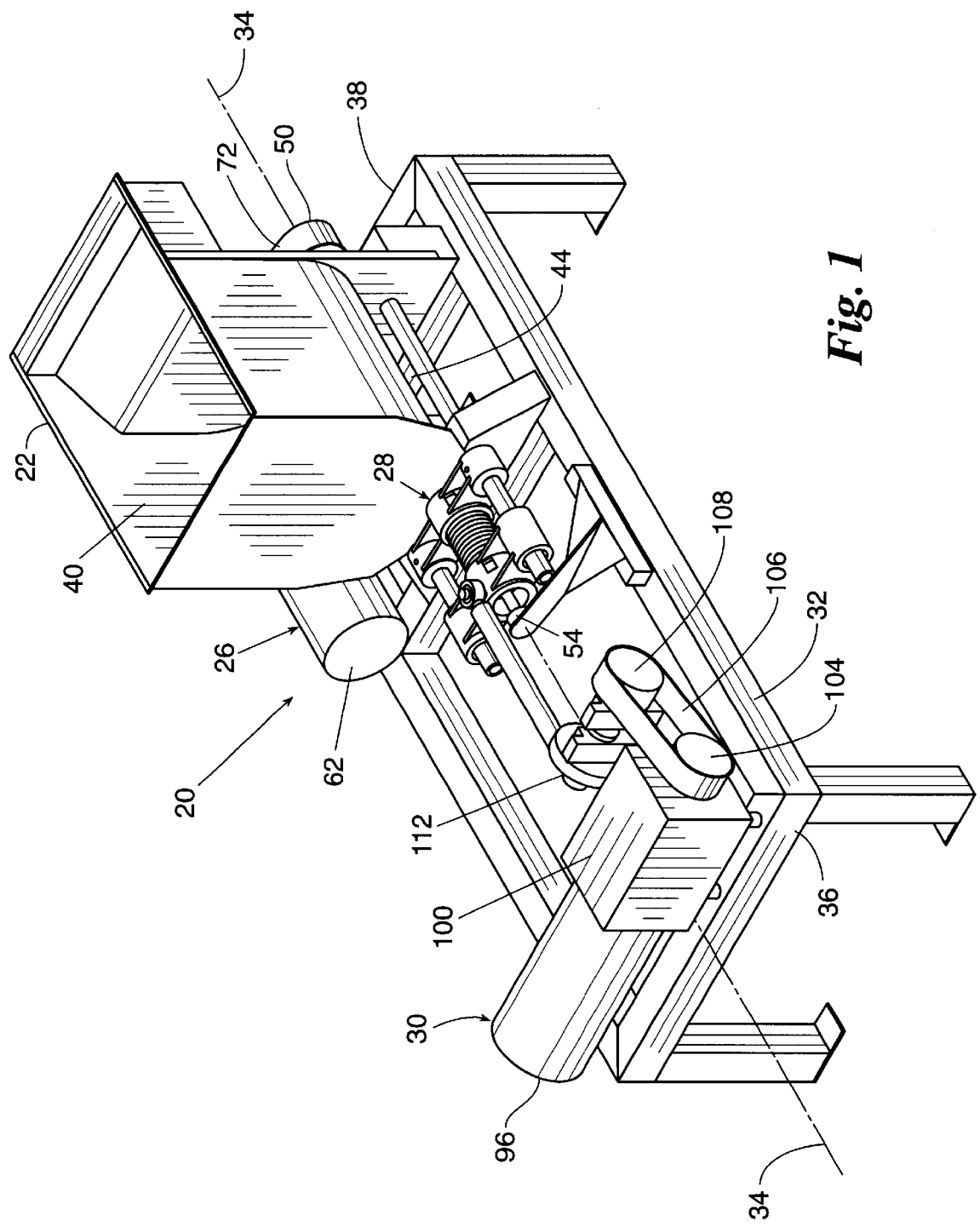
FIG. 1 provides a perspective view of the inventive spring cutter-separator in its general environment.
Figure 2:
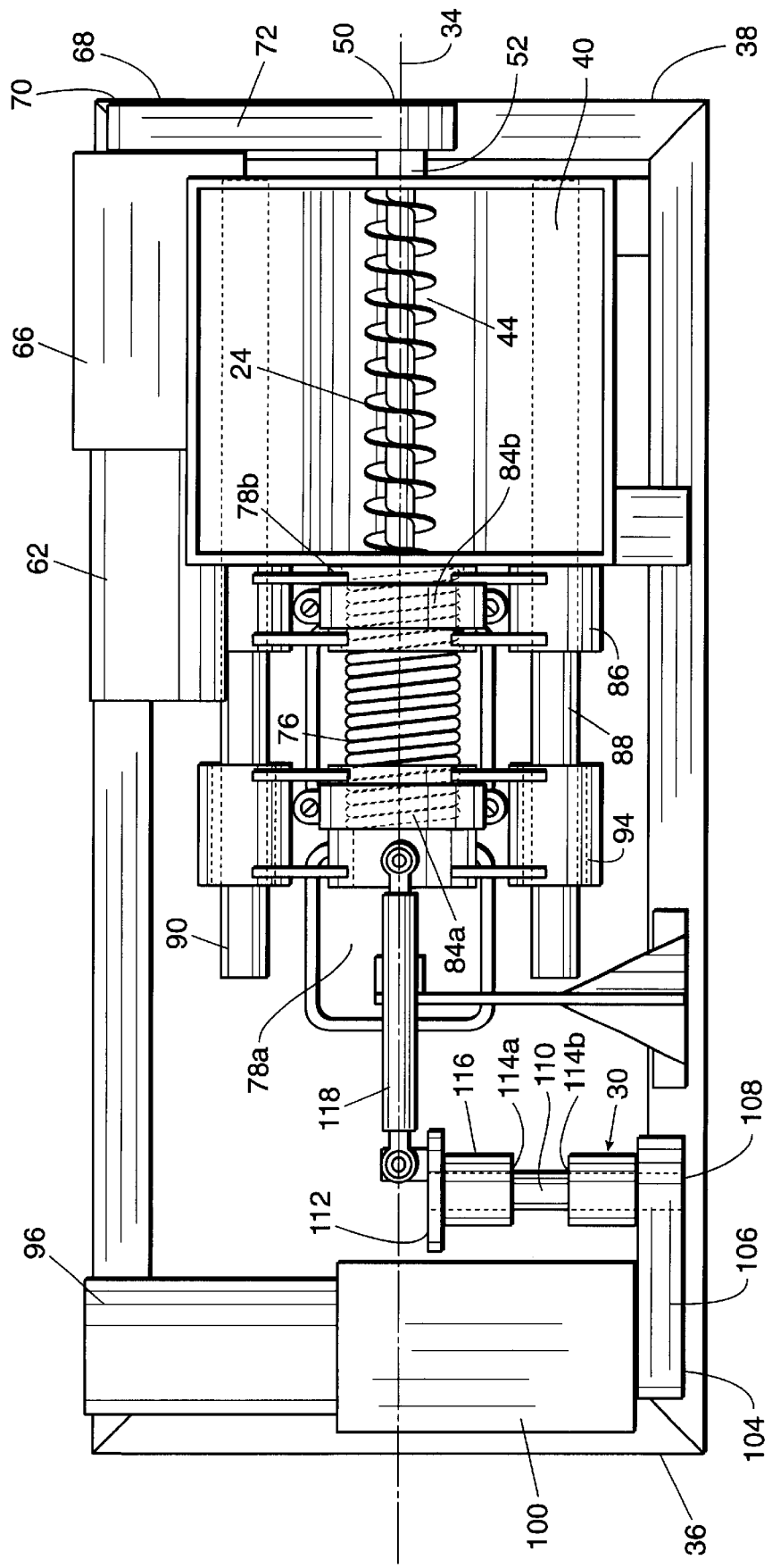
FIG. 2 provides a top elevational view of the inventive spring cutter-separator with the spring in its fully compressed state.
Figure 3:
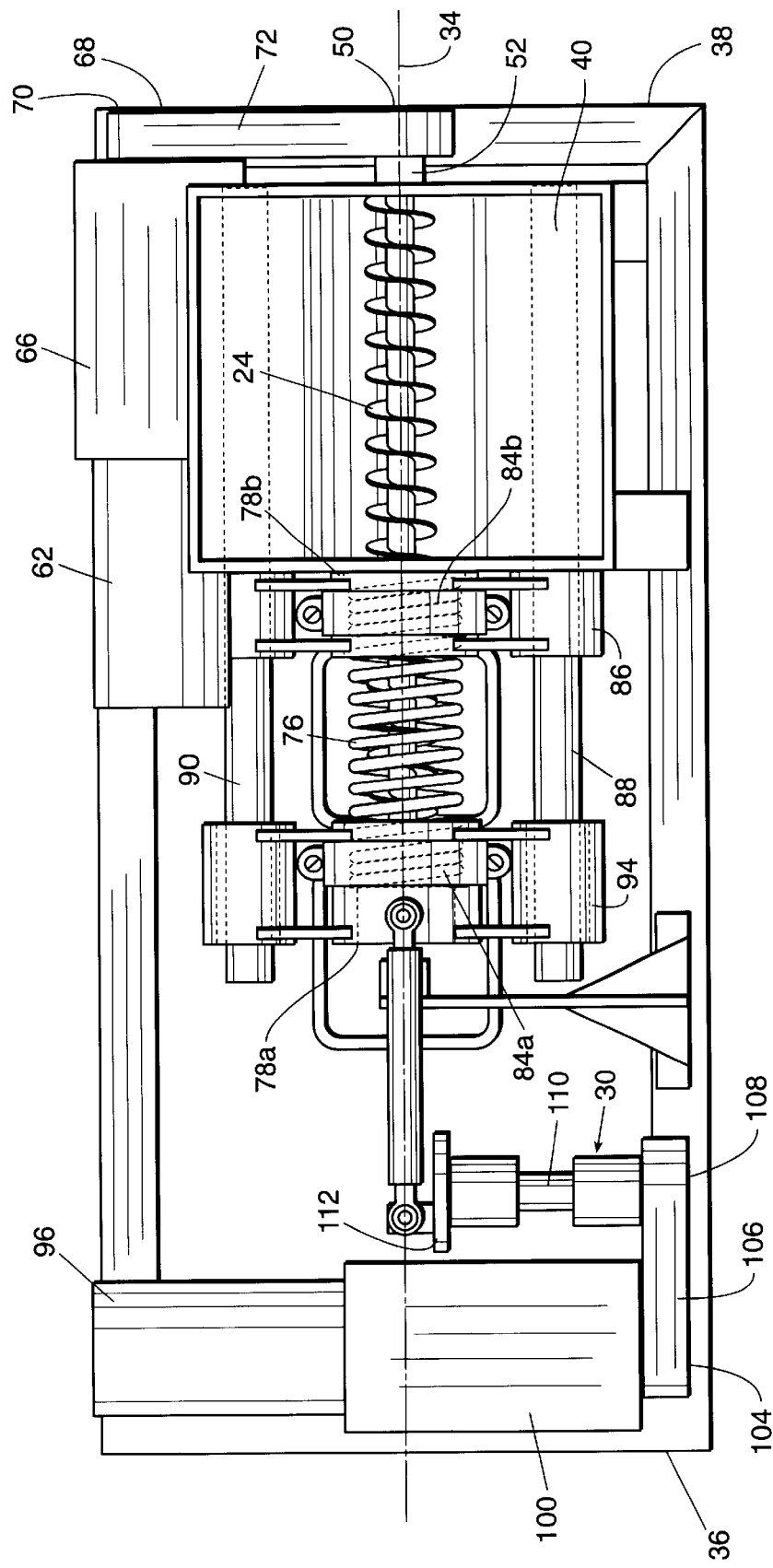
FIG. 3 provides a top elevational view of the inventive spring cutter-separator with the spring in its fully extended state.

Referring to FIGS. 1–3, a preferred embodiment of the inventive spring cutter-separator is shown in its general environment. Before explaining this embodiment in detail, however, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

With this in mind, spring cutter-separator 20 comprises hopper 22, auger 24, auger drive assembly 26, spring assembly 28, oscillator 30 and frame 32. Spring cutter-separator 20 has longitudinal axis 34 which is located in line with auger 24 and generally centered from side-to-side of frame 32. For purposes of description with reference to the drawings, spring cutter-separator 20 has left end 36 and right end 38.

Hopper 22 is fabricated from stainless steel and provides an opening at the top 40 for loading the inventive device with product for processing. The product is funneled into auger tube 44 at the bottom of hopper 22.

Figure 21:
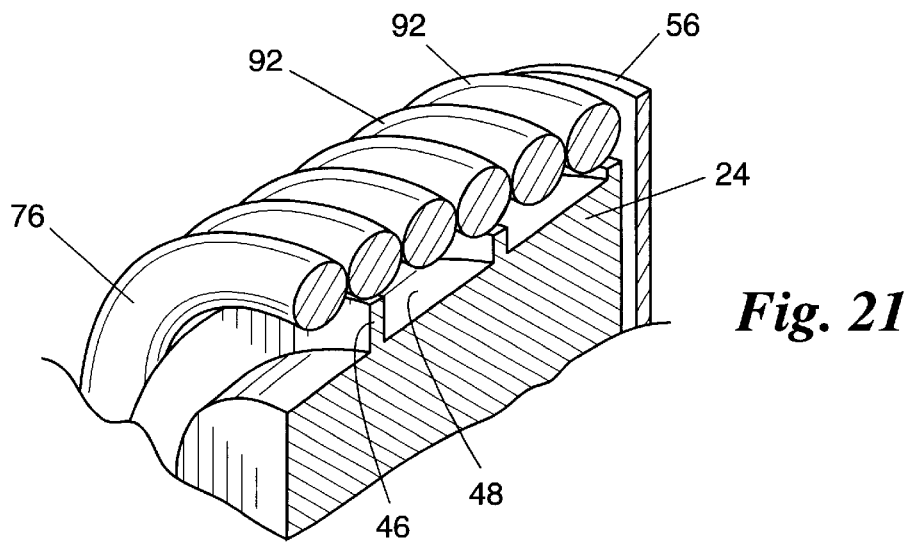
FIG. 21 provides a cross-sectional perspective view of the spring and auger incorporated in the inventive spring cutter-separator.
Figure 22:
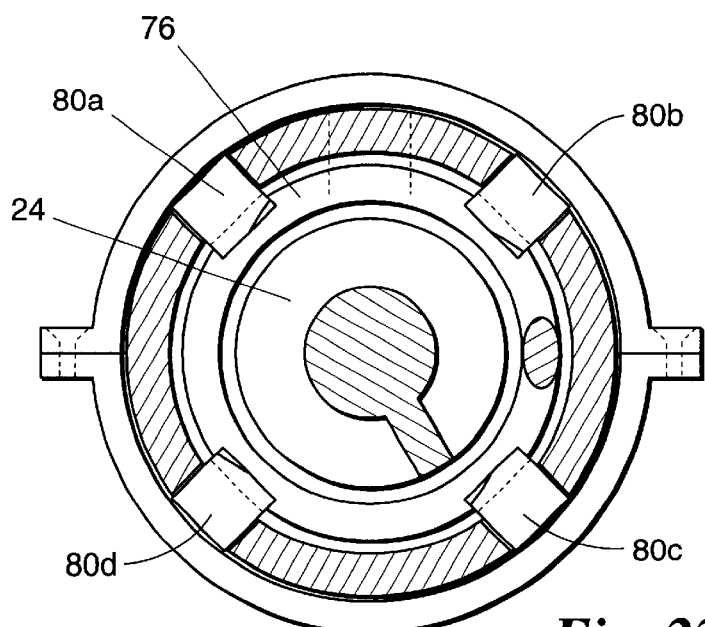
FIG. 22 provides a front view showing a spring coupler and wedge blocks installed in the inventive spring cutter-separator.

With further reference to FIG. 21, preferably, auger 24 comprises an outside surface 46 into which are formed spiral grooves 48 such that as auger 24 (FIGS. 2 and 3) rotates, product will be carried longitudinally along auger 24 by grooves 48. Pulley 50 is nonrotatably fixed to the end of auger 24 proximate the right end 38 of spring cutter-separator 20. Auger 24 extends from pulley 50, through bearing 52 which supports auger 24 between pulley 50 and hopper 22, through auger tube 44, through spring assembly 28, to bearing 54. Preferably, the depth of grooves 48 decreases along the length of auger 24 beneath spring assembly 28 such that as product is carried along auger 24 the product is forced into an ever decreasing space.

As will be apparent to those skilled in the art, auger 24 operating in conjunction with the auger tube 44 comprises a feeder for delivering material under pressure to the spring 76. Feeders are known in the art and generally include structure comprising an input supplying material through a pathway under pressure to an output end of the pathway. While the feeder of the preferred embodiment employs an auger to pressurize the product flow, other methods are equally well suited for the task, for example, a hydraulic or pneumatic press, ram or plunger could be used to generate the required pressure and create the product flow.

Figure 23:
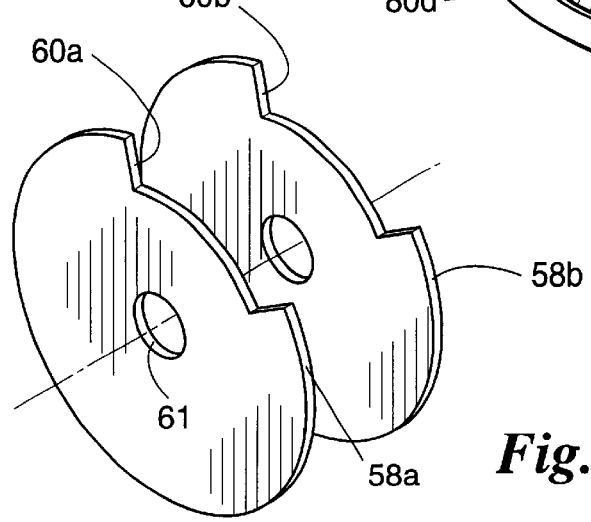
FIG. 23 provides a front view of an UHMW polyethylene disk as incorporated in the backpressure plate of the inventive spring cutter-separator.

To prevent the unrestricted flow of product from the outboard end of spring 76, auger 24 includes backpressure plate 56 (FIG. 21). As shown in FIG. 23, backpressure plate 56 comprises two disks 58a and b, each having slot 60a and 60b, respectively. Backpressure plate 56 is mounted to auger 24 through aperture 61 such that disk 58a is rotatable with respect to disk 58b. Thus, slot 60a may be either partially or fully aligned with slot 60b to form an adjustable aperture (not shown) through backpressure plate 56. Disks 58a and 58b are typically adjusted such that the largest expected contaminant particle will pass through the resulting aperture.

Auger drive assembly 26 includes auger drive motor 62 coupled to gear reducer 66. The output of gear reducer 66 is connected through pulley 70 and timing belt 72 to auger pulley 50. A variable speed drive (not shown) provides continuously variable control of auger speed.

Referring now to FIGS. 2, 3, 12, and 13, spring assembly 28 includes helical spring 76. Spring 76 is wound in a continuous coil, typically from stainless steel wire. In the preferred embodiment, spring 76 is wound such that, at rest, coils 92 remain completely closed, as depicted in FIGS. 2 and 13.

A first end of spring 76, is preferably connected to first spring coupler 78a by wedge blocks 80a–d (FIGS. 14–17) which are placed in corresponding apertures 82a–d (FIGS. 18–22) provided in coupler 78a and secured with band clamp 84a. Grooves 85 provided in wedge blocks 80a–d mate with coils 92 of spring 76 to secure coupler 78a to spring 76. Likewise, the other end of spring 76 is connected to second spring coupler 78b by wedge blocks 80e–h which are placed in corresponding apertures 82e–h provided in coupler 78b and secured with band clamp 84b. First spring coupler 78a is secured to spring anchor 60 which is non slidably located on guide rods 88 and 90 secured to frame 36. Second spring coupler 78b is secured to spring slider 94 which is slidably mounted to guide rods 88 and 90.

Oscillators to provide substantially linear reciprocating movement are known in the art. In the inventive apparatus, an oscillator includes a drive element connected to at least one end of spring 76 to reciprocatingly stretch spring 76 to provide extrusion of the material during the portion of an oscillator cycle wherein spring 76 is stretched, followed by separation of the extruded material during the portion of an oscillator cycle wherein spring 76 is compressed. Referring again to FIGS. 1, 2 and 3, preferably, oscillator 30 comprises spring drive motor 96 coupled to gear reducer 100. The output of gear reducer 100 drives pulley 104 and timing belt 106 which, in turn, drives pulley 108, shaft 110, and cam 112.

Shaft 110 is rotatably fixed to frame 32 by bearings 114a and 114b mounted in bracket 116. As best seen in FIGS. 2, 3, 12 and 13, as cam 112 rotates, drive element 118 converts the circular motion of cam 112 into a linear motion, alternately pushing and pulling spring slider 94 such that spring 76 is extended and compressed in an oscillating manner. As cam 112 rotates, one rotation of cam 112 produces one oscillation of spring 76.

It will be apparent to those skilled in the art that while the preferred embodiment has been discussed with reference to an oscillator comprising a rotating cam operating in conjunction with a drive element, the invention is not so limited.

By way of example and not limitation, the oscillator function could be provided by a hydraulic or pneumatic cylinder, a linear actuator, or the like.

To operate the inventive spring cutter-separator, backpressure plate 56 is adjusted to provide the minimum opening to provide passage of the largest expected contaminant. The auger drive motor 62 and spring drive motor 96 are turned on and the auger variable speed drive and spring variable speed drive are adjusted to the desired rates. Next, product such as food or agricultural products, which may contain dense contaminants such as bone, glass, plastic, or the like, are placed in hopper 22.

Rotating auger 24 draws product from the bottom of hopper 22, carrying the product through auger tube 44, and forcing it into spring assembly 28. As product is carried along auger 24, the pressure increases, forcing fluidized product to flow through the gaps between coils 92 of spring 76 while spring 76 is extended. As spring 76 oscillates, coils 92 compress, causing individual coils 92 to contact each other thereby cutting the product which has been extruded between the coils 92 of spring 76. Contaminants which are too large to pass between the individual coils 92 and too dense to fluidize, are carried by the spiral groove 48 of auger 24 to the end of spring 76 where they are discharged through the aperture formed by slots 60 in backpressure plate 56. As product is carried along auger 24, groove 48 is of ever decreasing depth such that the pressure of the product flow will remain substantially constant as product is discharged from the device through spring 76.

Discharged product may be processed by the inventive device several times, each processing operation resulting in a corresponding size reduction, until the product is of the desired size.

It will be apparent to those skilled in the art that while the preferred embodiment of the inventive device has been described with reference to a spring formed of wire with a circular cross section, virtually any configuration of spring wire could be used, such as wire of elliptical, oval, square, hexagonal, or other cross-sectional shape.

EXAMPLE

A spring cutter-separator was constructed as hereinbefore described. A suitable hopper and feeder were obtained from a used chopper (model 4346, Hobart Manufacturing Co., Troy, Ohio). The feeder consists of an auger 82.6 millimeters outside diameter and 0.61 meters long. The spiral groove was built-up over the last 200 millimeters of the output end of the auger such that the diameter measured at the bottom of the groove increased linearly from the original diameter of 38 millimeters to 76 millimeters at the terminus. This increasing diameter served to maintain a more uniform product pressure during processing.

An auger pulley was driven by a rubber timing belt that coupled to an 8:1 gear reducer (U.S. Drives; a division of Emerson Electric Co., St. Louis, Mo.) which, in turn, was driven by a three horsepower electric motor (U.S. Drives, a division of Emerson Electric Co., St. Louis Mo.). The motor was electrically driven using an electronic variable speed drive (model ACS 300, ABB, Inc., Norwalk, Conn.). This arrangement provided continuously variable auger speed from 0 to 225 rpm.

A helical spring was wound in a continuous coil from 12.7 millimeters diameter type 304 stainless steel wire. The spring wound such that, at rest the coils remained completely closed with an outside diameter of 114 millimeters and an overall length of 305 millimeters. The spring was attached to spring couplers, as described above, using four wedge blocks per spring.

A linkage was used to attach the movable end of the spring to a cam. As the cam rotates, the linkage pulls and pushes on the spring for a total stroke length of 63.5 millimeters. The theoretical separation between adjacent spring coils was 3.2 millimeters.

The cam was attached to a shaft with a pulley at the opposite end. The pulley was driven by a rubber timing belt coupled to an 8:1 gear reducer (U.S. Drives, a division of Emerson Electric Co., St. Louis, Mo.) which, in turn, was driven by a 7.5 horsepower electric motor (U.S. Drives, a division of Emerson Electric Co., St. Louis, Mo.). The motor was electrically driven using an electronic variable speed drive (model ACS 600, ABB3, Inc., Norwalk, Conn.). This arrangement provided continuously variable spring cycle rates from 0 to 225 cycles per minute (corresponding to cam shaft rotational speeds of 0 to 225 rpm).

The backpressure plate was constructed from two 6.4 millimeter thick, Ultra High Molecular Weight (UHMW) polyethylene disks stacked and mounted on a shaft protruding from the center of the outboard end of the auger. Each disk included a slot on its periphery, 9.5 millimeters deep with sides extending at 45 degrees.

The support frame was constructed from mild steel and casters were mounted on each leg. The frame under the spring assembly was open to allow product and materials discharged from the spring and auger to freely fall into separate containers placed on carts below the unit.

Experimental Results

Tests were performed on the device constructed in the above Example by processing chunks of beef which had initially been cut by hand into pieces which were roughly cube shaped, approximately 20 millimeters on a side and weighing approximately 85 grams each. Processing was performed on 5.0 kg batches of chunks. For each batch, the device was operated at constant settings until an entire batch had been processed.

In a first series of tests, the spring was cycled at 25, 50, 75, an 100% of rated speed (56, 113, 169, and 225 cycles per minute, respectively) while the auger speed was held constant at 50% of rated speed (113 rpm). In a second series of tests, the spring was cycled at a constant rate of 50% of rated speed (113 cycles per minute) while the auger speed was set at 25, 50, 75, and 100% of rated speed (56, 113, 169, and 225 rpm, respectively). Meat collected at the spring and backpressure plate was weighed separately. After each batch of meat was processed and the data recorded, the meat was returned to the hopper for reprocessing. The reprocessing procedure was repeated three times for each set of experimental conditions.

Separation efficiency was tested using 7.94, 6.10, and 4.76 millimeter ball bearings. Ball bearings were selected since they are commonly available in various sizes and their spherical shape has no effect on the separation process. In separate tests, ten ball bearings of the same size were added at random positions to the meat chunks in the hopper. Following processing, the meat discharged from the spring and the backpressure plate was inspected by hand and the bearings were identified and counted. Two repetitions were repeated for each bearing size.

The results of the tests are shown in graphical form in FIGS. 4–11. When the auger speed was set at 25% (56 rpm), the meat chunks would not feed into the cutter-separator on the first and second processing cycles. When the auger speed was set at 50% (113 rpm), meat would not reliably feed on the first processing, however, the meat would reliably feed on subsequent reprocessing cycles. No feeding problems were encountered at auger speeds of 75 and 100% (169 and 225 rpm respectively).

Figure 4:
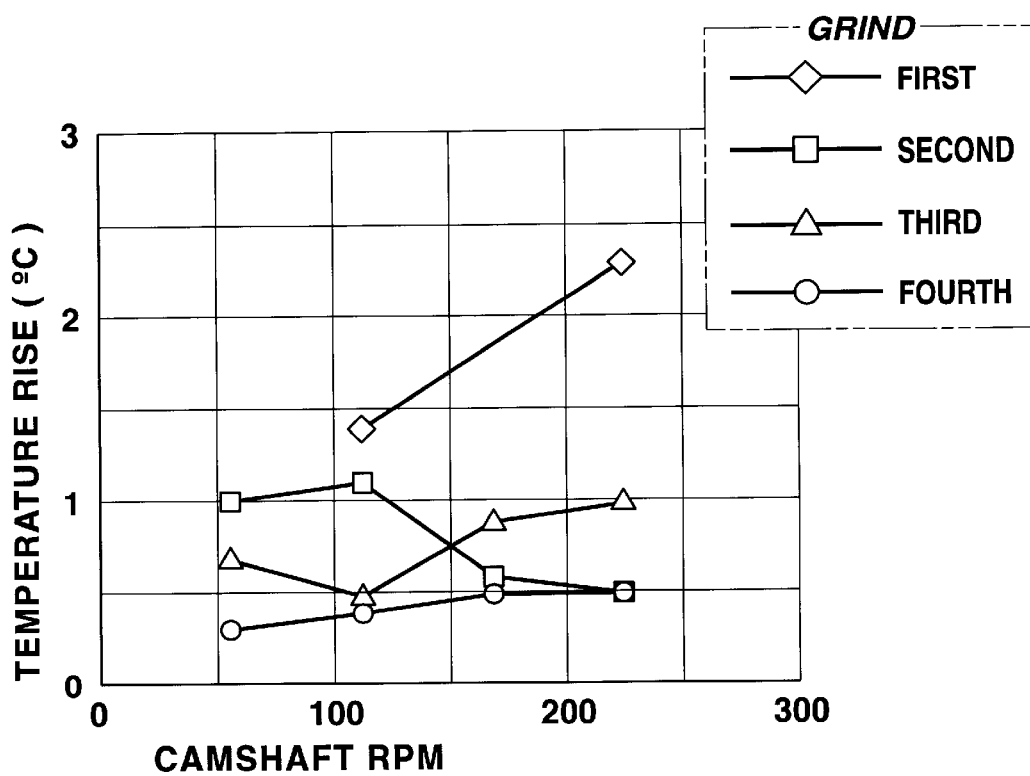
FIG. 4 shows representative temperature rise in product when processed by the preferred embodiment of the inventive spring cutter-separator at various oscillation rates of the spring.
Figure 5:
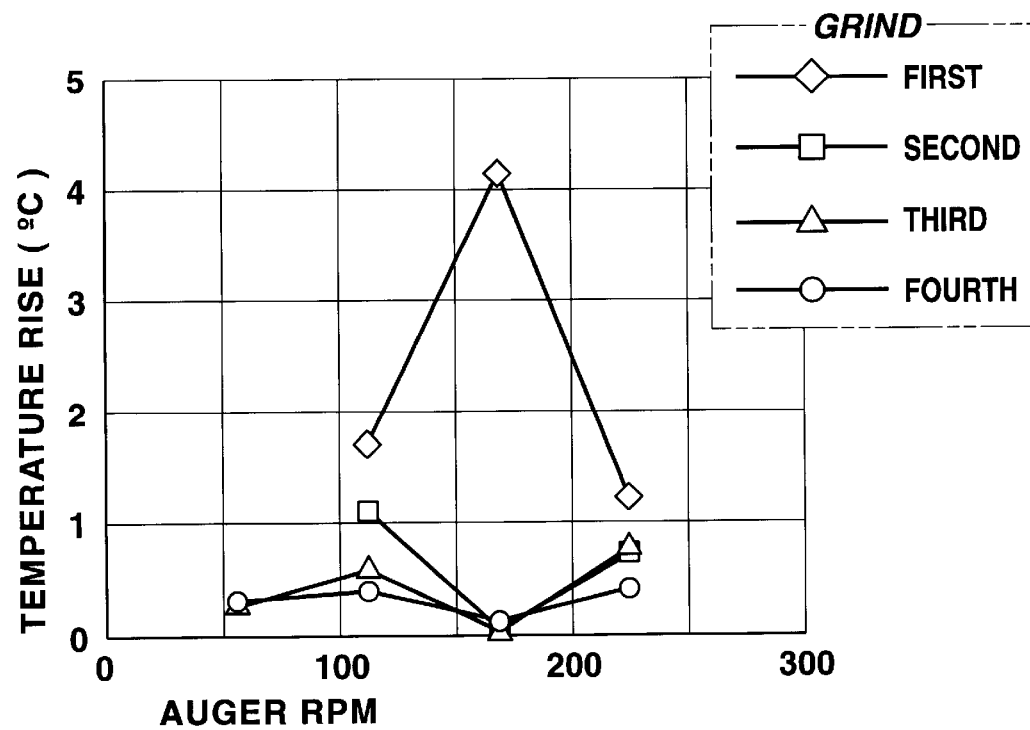
FIG. 5 shows representative temperature rise in product when processed by the preferred embodiment of the inventive spring cutter-separator at various auger speeds.

Temperature rise, as shown in FIGS. 4 and 5, was measured within 1.0° C. using, a handheld, piercing thermocouple. Temperature rise is the temperature difference between the temperature of the bulk meat immediately after processing and the temperature of the bulk meat in the hopper immediately prior to processing. FIG. 4 shows temperature rise for the product exiting the spring with respect to spring camshaft rpm. The first processing resulted in a temperature rise slightly over 2° C. Reprocessing cycles resulted in a temperature rise of 1° C. or less.

FIG. 5 shows temperature rise in product exiting the backplate with respect to auger speed. The first processing resulted in a temperature rise as much as 4° C. Reprocessing cycles resulted in a temperature rise of 1° C. or less.

Figure 6:
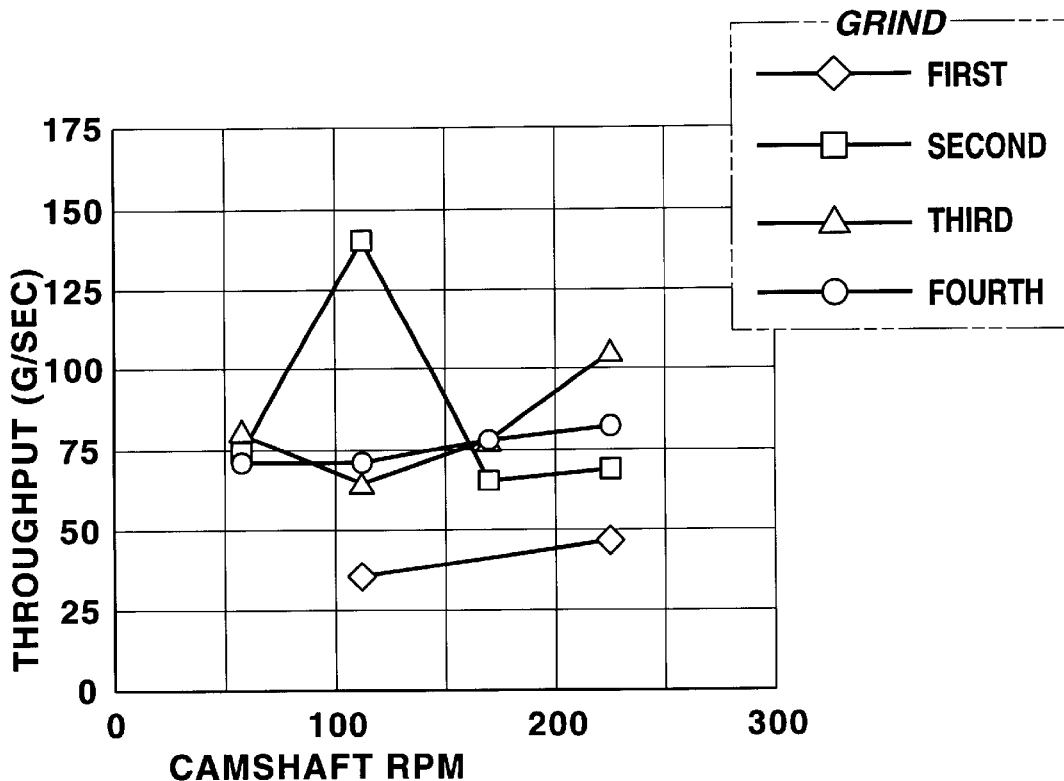
FIG. 6 shows representative troughput of the preferred embodiment of the inventive cutter-separator at various oscillation rates of the spring.
Figure 7:
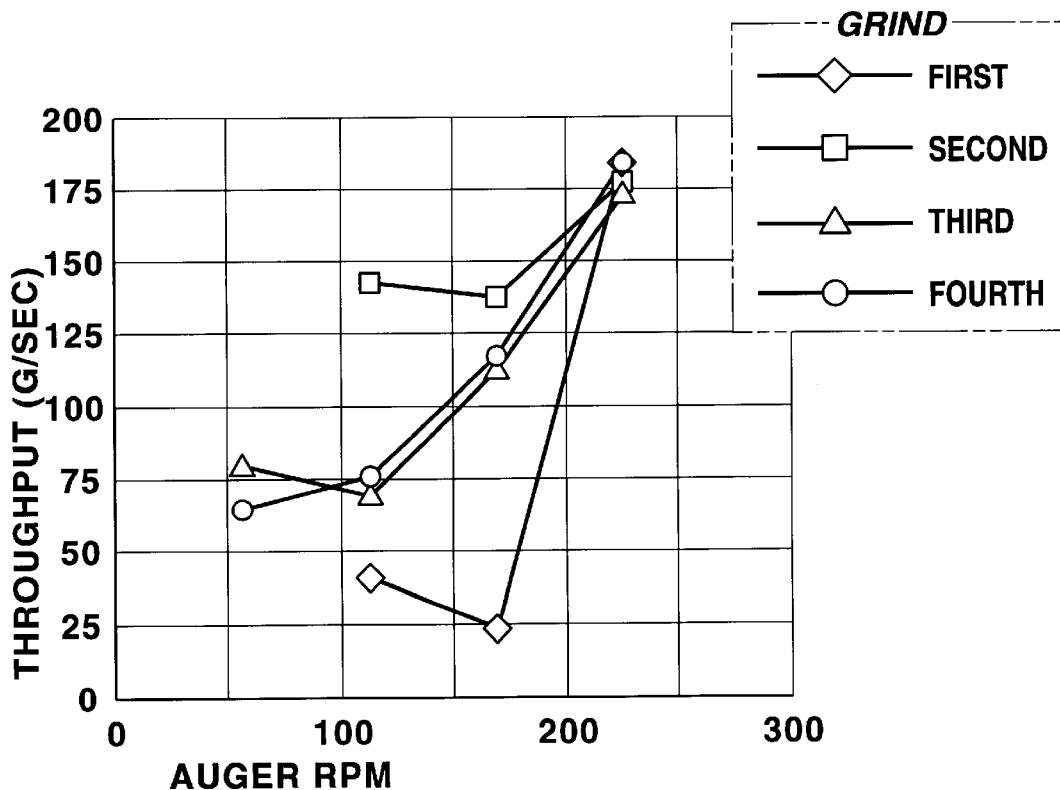
FIG. 7 shows representative throughput of the preferred embodiment of the inventive spring cutter-separator at various auger speeds.

Mass throughput, as shown in FIGS. 6 and 7, was examined by timing runs at fixed machine settings and measuring the mass outputs at the spring and backpressure plate. FIG. 6 shows mass throughput plotted with respect to spring camshaft speed (rpm) at a constant auger speed of 113 rpm. FIG. 7 shows mass throughput with respect to auger speed while spring camshaft speed was maintained at 113 rpm. Comparing FIGS. 6 and 7, it can be seen that the effect of auger speed on throughput is more dramatic than the effect of spring cutter cam speed.

Throughput Mass Ratio ("TMR") is defined as the ratio of the meat discharged at the spring divided by the mass of the meat discharged at the backpressure plate. Magnitude of the TMR is an indication of the operational efficiency of the inventive device, since materials discharged at backpressure plate may include valuable product along with separated contaminants or unwanted materials (such as gristle in the case of meats). Materials discharged at the backpressure plate could be recycled, depending upon the process, product, and the desired results. In the case of meat products, it is desirable to maximize the TIMR in a range that produces the greatest amount of salable product while effectively removing contaminants.

Figure 8:
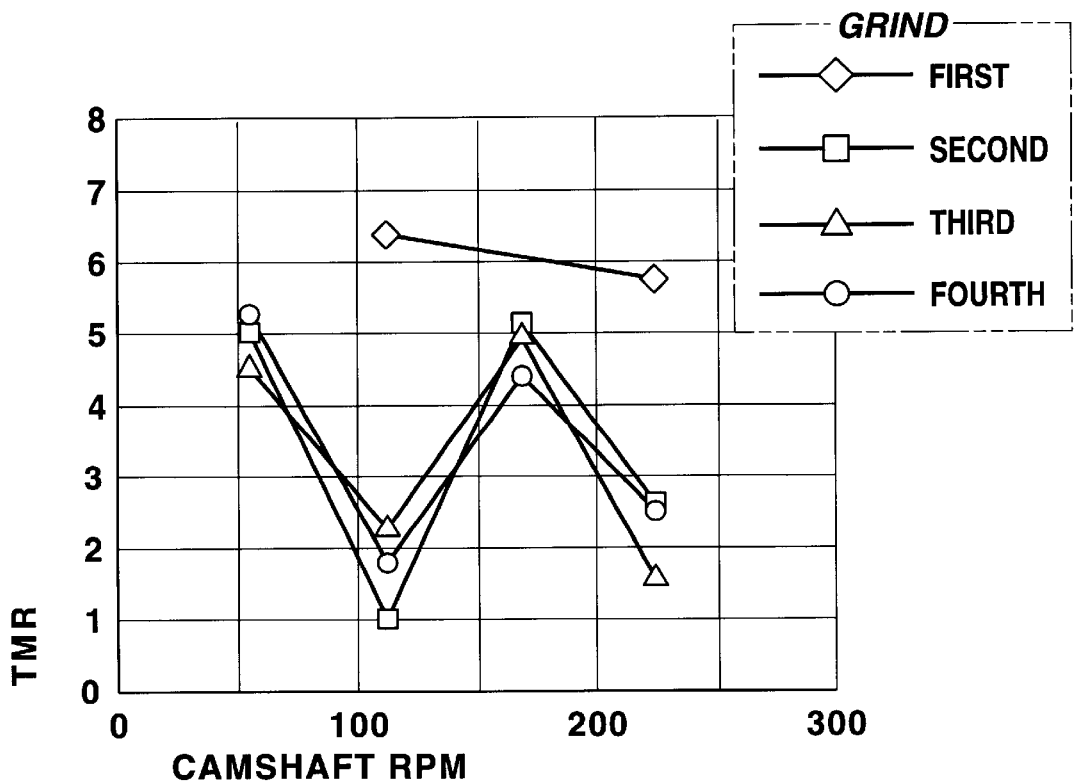
FIG. 8 shows representative throughput mass ratio of the preferred embodiment of the inventive spring cutter-separator at various oscillation rates of the spring.
Figure 9:
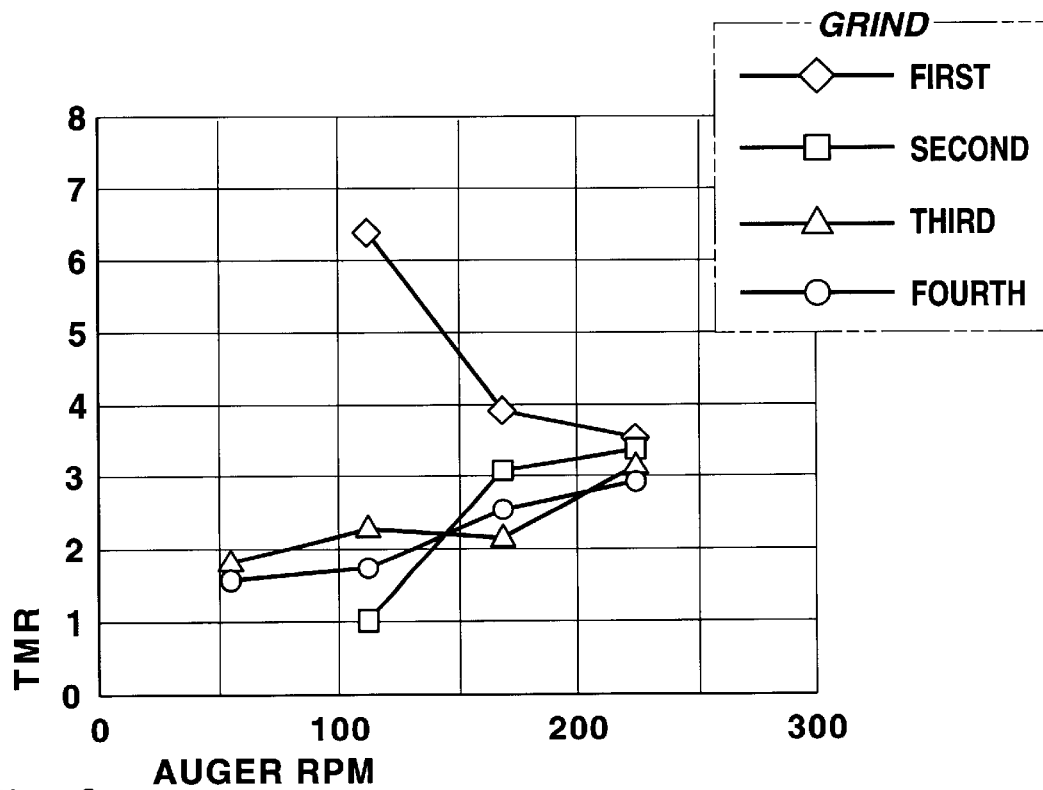
FIG. 9 shows representative throughput mass ratio of the preferred embodiment of the inventive spring cutter-separator at various auger speeds.

FIG. 8 shows TMR plotted against spring camshaft speed (rpm) at a constant auger rate of 113 rpm. FIG. 9 shows TMR versus auger speed (rpm) at a constant spring cutter camshaft speed of 113 rpm. FIG. 8 shows an interaction between spring camshaft rate and TMR. FIG. 9 shows a general improvement in TMR with increased auger speed.

Figure 10:
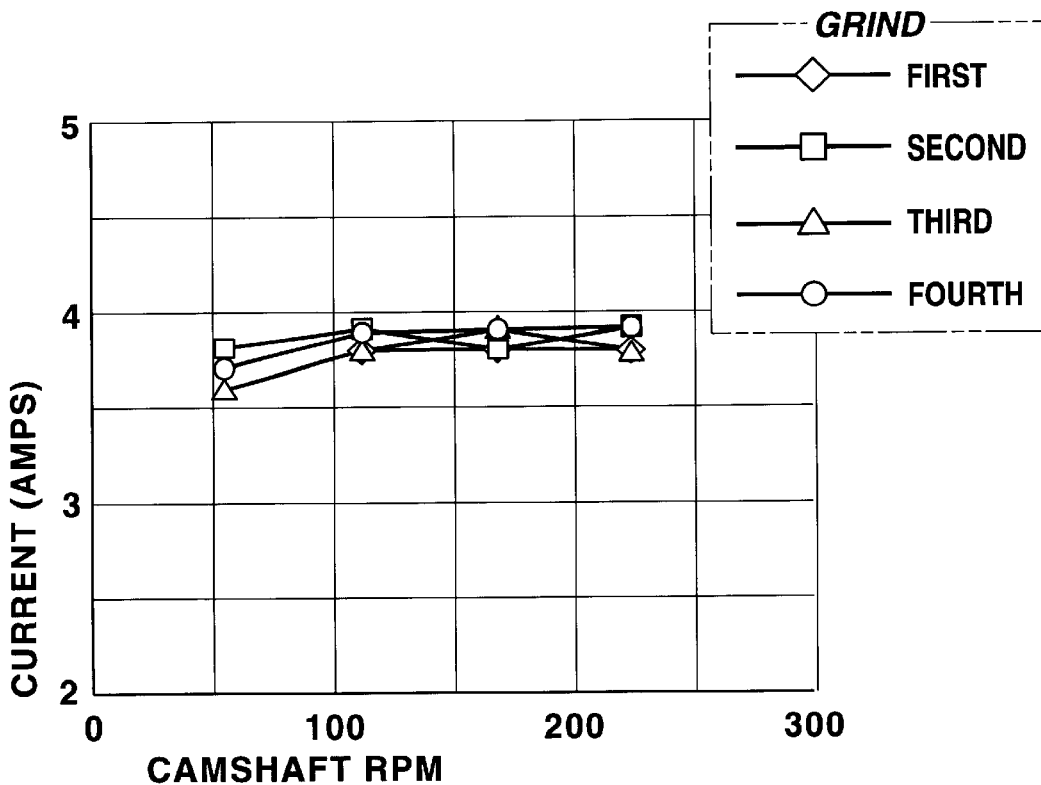
FIG. 10 shows electrical current requirements for the preferred embodiment of the inventive spring cutter-separator over a range of oscillation rates of the spring.

FIG. 10 shows spring motor current draw relative to spring camshaft speed (rpm) at an auger speed of 113 rpm. Power consumption is the product of voltage multiplied by the electrical current draw in amps. Since the voltage was fixed at 460 volts for all tests, power consumption of the drive units was directly proportional to the current draw. As can be seen in FIG. 10, the current and thus, the power remained substantially constant over the range tested.

Figure 11:
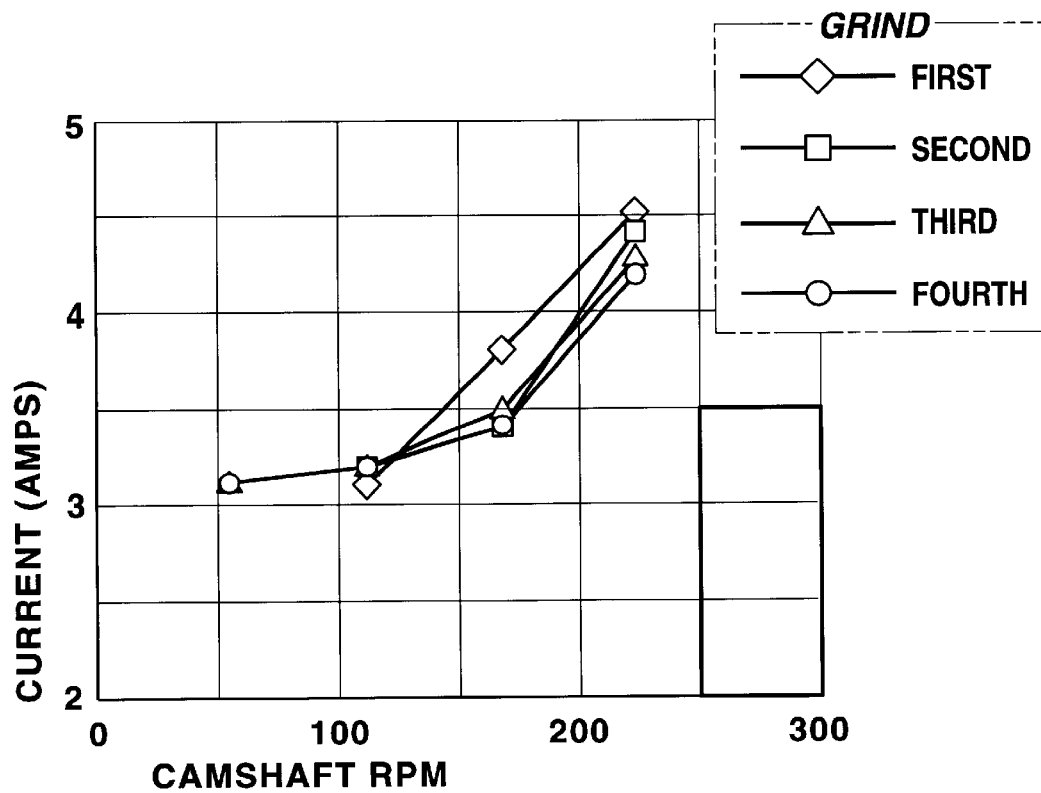
FIG. 11 shows the electrical current requirements for the preferred embodiment of the inventive spring cutter-separator over a range of auger speeds.
Figure 18:
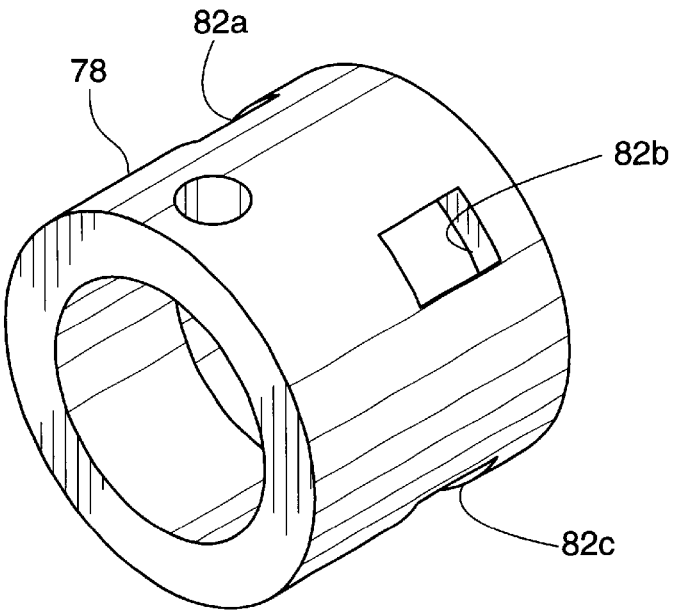
FIG. 18 provides a perspective view of a spring coupler as incorporated in the inventive spring cutter-separator.
Figure 20:
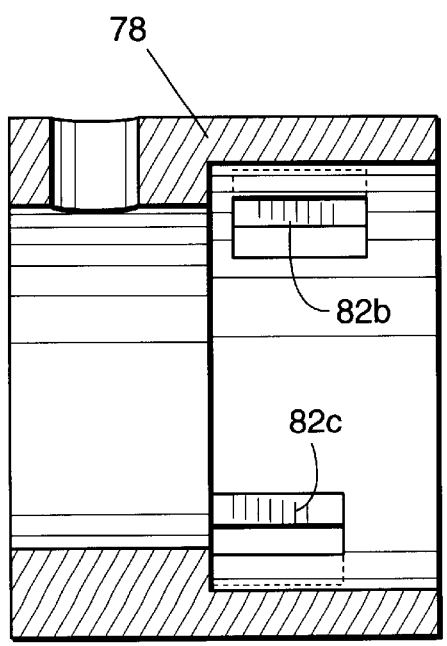
FIG. 20 provides a side cutaway view of a spring coupler as incorporated in the inventive spring cutter-separator.
Figure 19:
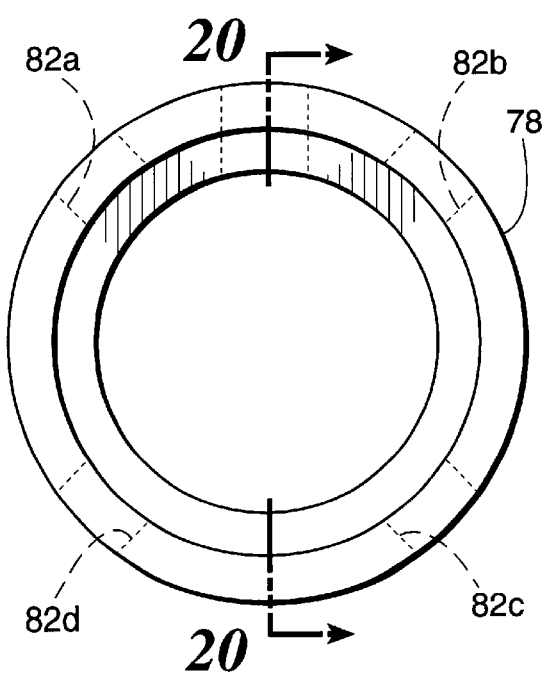
FIG. 19 provides a front view of a spring coupler as incorporated in the inventive spring cutter-separator.

FIG. 11 provides a plot of auger motor current draw versus auger speed (rpm), while the spring camshaft speed was held constant at 113 rpm. FIG. 11 shows an increase in current draw and, therefore, power consumption as the speed of the auger is increased.

Separation tests revealed complete separation for ball bearings with a diameter equal to or greater than the greatest opening between coils of the spring when fully extended. In practice, the openings between the individual coils of the spring are not uniform along the entire length of the spring. These openings varied from nearly zero to 5 millimeters. For both tests of the 7.94 millimeter bearings and both tests of the 6.10 millimeter bearings, ten out of ten bearings were separated. Some of the 4.76 millimeter bearings were discharged at the spring cutter; four during the first test and two during the second test. One of the 4.76 millimeter bearings was unaccounted for on the first test.

It will also be apparent to those skilled in the art that while in the above example, the inventive device was used to process meat, its operation applies equally well to a variety of food and agricultural products including, by way of example and not limitation, fruits, grains and vegetables.

It will also be apparent to those skilled in the art that the inventive spring cutter-separator could be used to separate seeds, stems, hulls, and the like from desirable product.

Thus, the present invention is well adapted to carry out the objects and attain the ends and advantages mentioned above as well as those inherent therein. While presently preferred embodiments have been described for purposes of this disclosure, numerous changes and modifications will be apparent to those skilled in the art. Such changes and modifications are encompassed within the spirit of this invention.

What is claimed is:

1. An apparatus for separating desirable matter from undesirable matter, comprising:
   a spring having a bore extending longitudinally therethrough and comprising a plurality of coils, at least one end of said spring being connected for linear reciprocation to an oscillator, wherein when said spring is in a compressed state said coils are in close proximity and when in an extended state there is created a plurality of gaps between said coils; and
   a feeder adjacent a first end of said bore to supply a mixture of desirable matter and undesirable matter into and through said bore at a predetermined pressure, the undesirable matter being of a size larger than the size of said gaps;
   whereby the desirable matter is extruded between said coils as said spring is extended while the undesirable matter is carried through said bore of said spring to be discharged at a second end thereof.

2. The apparatus according to claim 1, wherein said spring is a helical spring comprising a continuous coil.

3. The apparatus according to claim 2, wherein said spring is formed of a stainless steel wire.

4. The apparatus according to claim 1, wherein said spring is of a circular cross section.

5. The apparatus according to claim 1 further comprising:
   a backpressure plate positioned at said second end of said spring, said plate possessing an aperture through which the undesirable matter is discharged.

6. The apparatus according to claim 5, wherein the size of said aperture is adjustable.

7. The apparatus according to claim 6, wherein said backpressure plate comprises two adjacent disks in rotatable relation, each having a slot thereon, whereby the slots may be partially or fully aligned to form an adjustable aperture.

8. The apparatus according to claim 1, wherein said pressure is sufficient to fluidize the desirable matter.

9. The apparatus according to claim 1 wherein said feeder includes an auger rotatably positioned within said bore.

10. The apparatus according to claim 9, wherein said auger possesses a flighting and grooves formed between said flighting, the depth of said grooves decreasing along the length of said auger toward the discharge end of said spring.

* * * * *